(12) United States Patent
Mijers et al.

(10) Patent No.: US 7,673,653 B2
(45) Date of Patent: Mar. 9, 2010

(54) CHECK VALVE

(75) Inventors: Jan W. M. Mijers, Heemstede (NL); Brendan Hogan, Gort (IE); Kieran Costello, Co. Tipperary (IE); Colm Carmody, Co. Kerry (IE); Brendan Casey, Co. Tipperary (IE)

(73) Assignee: Filtertek Inc., Hebron, IL (US)

( * ) Notice: Subject to any disclaimer, the term of this patent is extended or adjusted under 35 U.S.C. 154(b) by 123 days.

(21) Appl. No.: 11/638,954

(22) Filed: Dec. 14, 2006

(65) Prior Publication Data

US 2007/0163664 A1 Jul. 19, 2007

Related U.S. Application Data

(63) Continuation-in-part of application No. PCT/EP2005/006425, filed on Jun. 17, 2005.

(30) Foreign Application Priority Data

Jun. 17, 2004 (DE) .................. 20 2004 009 521 U
Oct. 30, 2006 (DE) .................. 20 2006 016 730 U

(51) Int. Cl.
*F16K 15/14* (2006.01)
(52) U.S. Cl. ................... 137/859; 137/843; 137/852
(58) Field of Classification Search ............ 137/843, 137/852, 854, 859
See application file for complete search history.

(56) References Cited

U.S. PATENT DOCUMENTS

| | | | |
|---|---|---|---|
| 2,630,874 A | 3/1953 | Langdon | |
| 2,758,609 A | 8/1956 | Dickert et al. | |
| 2,980,032 A | 4/1961 | Schneider | |
| 3,084,707 A | 4/1963 | Frye | |
| 3,238,056 A | 3/1966 | Pall et al. | |
| 3,270,771 A | 9/1966 | Morgan et al. | |
| 3,599,657 A | 8/1971 | Maldays | |
| 3,623,504 A | 11/1971 | Davis | |
| 3,633,605 A | 1/1972 | Smith | |
| 3,658,183 A | 4/1972 | Best et al. | |
| 3,779,274 A | 12/1973 | Kelly | |
| 3,782,083 A | 1/1974 | Rosenberg | |
| 3,794,043 A | 2/1974 | McGinnis | |
| 3,932,153 A | 1/1976 | Byrns | |
| 3,966,520 A | 6/1976 | Fallenbeck et al. | |
| 4,022,258 A | 5/1977 | Steidley | |
| 4,089,349 A | 5/1978 | Schenk | |

(Continued)

FOREIGN PATENT DOCUMENTS

BE 1 009 834 A6 10/1997

(Continued)

OTHER PUBLICATIONS

"Design for assembly"; http://web.archive.org/web/20021026013912/http://www.scudc.scu.edu/cmdoc/dg_doc/develop/design/part/33000004.htm; Allegedly archived Oct. 26, 2002; 10 pages.

(Continued)

*Primary Examiner*—John Rivell
*Assistant Examiner*—Atif H Chaudry
(74) *Attorney, Agent, or Firm*—Brinks Hofer Gilson & Lione

(57) ABSTRACT

A check valve is provided, including a first hose connector housing defining an entry passage extending into an entry space at least partially defined by an annular valve seat, a second hose connector housing coupled with the first hose connector housing and defining an exit passage, and a generally flexible perforated membrane disk positioned between the first and second hose connector housings such that the membrane disk selectively engages the valve seat.

18 Claims, 6 Drawing Sheets

U.S. PATENT DOCUMENTS

| | | |
|---|---|---|
| 4,141,379 A | 2/1979 | Manske |
| 4,148,732 A | 4/1979 | Burrow et al. |
| 4,181,477 A | 1/1980 | Litt |
| 4,188,978 A | 2/1980 | DeLorenzo |
| 4,237,880 A | 12/1980 | Genese |
| 4,241,756 A | 12/1980 | Bennett et al. |
| 4,343,305 A | 8/1982 | Bron |
| 4,355,639 A | 10/1982 | Di Salvo |
| 4,404,006 A | 9/1983 | Williams et al. |
| 4,415,003 A | 11/1983 | Paradis et al. |
| 4,459,139 A | 7/1984 | von Reis et al. |
| 4,534,764 A | 8/1985 | Mittleman et al. |
| 4,556,086 A | 12/1985 | Raines |
| 4,593,720 A | 6/1986 | Bergandy |
| 4,630,606 A | 12/1986 | Weerda et al. |
| 4,646,781 A | 3/1987 | McIntyre |
| 4,664,800 A | 5/1987 | Raines et al. |
| 4,670,510 A | 6/1987 | Kobayashi et al. |
| 4,712,583 A | 12/1987 | Pelmulder et al. |
| 4,749,003 A | 6/1988 | Leason |
| 4,754,889 A | 7/1988 | Debetencourt |
| 4,768,547 A | 9/1988 | Danby et al. |
| 4,793,503 A | 12/1988 | Towns et al. |
| 4,825,862 A | 5/1989 | Sato et al. |
| 4,846,215 A | 7/1989 | Barree |
| 4,874,513 A | 10/1989 | Chakraborty et al. |
| 4,958,661 A * | 9/1990 | Holtermann et al. ......... 137/843 |
| 4,966,199 A * | 10/1990 | Ruschke .................... 137/843 |
| 4,986,905 A | 1/1991 | Bugar et al. |
| 5,011,555 A | 4/1991 | Sager |
| 5,025,829 A | 6/1991 | Edwards et al. |
| 5,041,105 A | 8/1991 | D'Alo et al. |
| 5,125,522 A | 6/1992 | Pezzoli et al. |
| 5,147,545 A | 9/1992 | Despard et al. |
| 5,215,538 A | 6/1993 | Larkin |
| 5,230,727 A | 7/1993 | Pound et al. |
| 5,265,770 A | 11/1993 | Matkovich et al. |
| 5,269,917 A | 12/1993 | Stankowski |
| 5,443,723 A | 8/1995 | Stankowski et al. |
| 5,453,097 A | 9/1995 | Paradis |
| 5,500,003 A | 3/1996 | Guala et al. |
| 5,505,326 A | 4/1996 | Junko |
| 5,520,661 A | 5/1996 | Lal et al. |
| 5,556,541 A | 9/1996 | Ruschke |
| 5,603,792 A | 2/1997 | Guala et al. |
| 5,617,897 A * | 4/1997 | Myers ....................... 137/859 |
| 5,695,638 A | 12/1997 | Gutiz et al. |
| 5,749,861 A | 5/1998 | Guala et al. |
| 5,771,935 A | 6/1998 | Myers |
| 5,782,383 A | 7/1998 | Robinson |
| 5,935,100 A | 8/1999 | Myers |
| 6,086,762 A | 7/2000 | Guala |
| 6,168,653 B1 | 1/2001 | Myers |
| 6,290,682 B1 | 9/2001 | Myers |
| 6,464,870 B1 | 10/2002 | Castellanos et al. |
| 6,579,342 B2 | 6/2003 | Wang |
| 6,708,714 B1 | 3/2004 | Mijers |
| 6,779,669 B2 | 8/2004 | Schann |
| 2002/0144595 A1 | 10/2002 | Wang et al. |
| 2003/0089409 A1* | 5/2003 | Morimoto ................... 137/859 |
| 2004/0074925 A1 | 4/2004 | Faurie |
| 2004/0153047 A1 | 8/2004 | Blank et al. |

FOREIGN PATENT DOCUMENTS

| | | |
|---|---|---|
| DE | 48105 | 6/1888 |
| DE | 667 675 | 4/1934 |
| DE | 1 695 553 | 5/1971 |
| DE | 1 675 370 | 9/1971 |
| DE | 25 02 673 A1 | 7/1976 |
| DE | 25 13 350 A1 | 10/1976 |
| DE | 27 13 618 C2 | 10/1977 |
| DE | 29 19 343 A1 | 11/1980 |
| DE | 30 35 301 A1 | 4/1981 |
| DE | 29 49 262 A1 | 6/1981 |
| DE | G 82 14 927.5 U1 | 9/1982 |
| DE | 32 15 329 A1 | 12/1982 |
| DE | 33 27 342 A1 | 2/1985 |
| DE | 34 35 900 A1 | 4/1986 |
| DE | G 86 03 917.2 U1 | 5/1986 |
| DE | 36 32 412 A1 | 3/1988 |
| DE | 38 03 380 A1 | 8/1989 |
| DE | 40 39 814 A1 | 6/1992 |
| DE | G 92 09 491 U1 | 10/1992 |
| DE | 41 42 494 A1 | 7/1993 |
| DE | 42 01 258 A1 | 7/1993 |
| DE | G 93 19 810.8 U1 | 3/1994 |
| DE | 43 09 262 A1 | 6/1994 |
| DE | 43 04 949 A1 | 8/1994 |
| DE | G 93 10 673.4 U1 | 9/1994 |
| DE | 43 15 701 A1 | 11/1994 |
| DE | G 295 01 239.0 U1 | 4/1995 |
| DE | 691 09 240 T2 | 10/1995 |
| DE | G 196 05 217.3 | 2/1996 |
| DE | G 296 10 419.1 | 12/1996 |
| DE | 195 45 421 A1 | 6/1997 |
| DE | 196 43 360 C1 | 5/1998 |
| DE | 197 49 562 C1 | 4/1999 |
| DE | 195 45 421 C2 | 5/2001 |
| DE | 102 19 994 A1 | 12/2003 |
| DE | 20 2004 009 521 U1 | 10/2004 |
| DE | 10 2004 053 214 A1 | 1/2006 |
| EP | 0 072 800 B1 | 3/1983 |
| EP | 0 379 047 A1 | 7/1990 |
| EP | 0 459 498 A1 | 12/1991 |
| EP | 0 562 246 A1 | 9/1993 |
| EP | 0 162 537 | 8/1994 |
| EP | 0 612 537 A2 | 8/1994 |
| EP | 0 612 537 A3 | 8/1994 |
| EP | 0 652 018 B1 | 5/1995 |
| EP | 0 812 596 A1 | 12/1997 |
| EP | 0 878 628 A2 | 11/1998 |
| EP | 0 887 085 A2 | 12/1998 |
| EP | 0 934 757 A2 | 8/1999 |
| EP | 1 063 956 B1 | 1/2001 |
| EP | 1 088 765 A1 | 4/2001 |
| EP | 1 093 828 A2 | 4/2001 |
| EP | 1 099 457 A2 | 5/2001 |
| EP | 1 239 145 B1 | 5/2007 |
| FR | 2 666 745 A1 | 3/1992 |
| GB | 439 278 A1 | 12/1935 |
| GB | 439278 | 12/1935 |
| GB | 811 818 | 4/1959 |
| GB | 2 027 168 A1 | 2/1980 |
| NL | 293686 | 4/1965 |
| WO | WO 88/02639 | 4/1988 |
| WO | WO 89/02764 | 4/1989 |
| WO | WO 91/11641 | 8/1991 |
| WO | WO 93/10015 A1 | 5/1993 |
| WO | WO 96/03166 A1 | 2/1996 |
| WO | WO 97/03712 | 2/1997 |
| WO | WO 97/47339 | 12/1997 |

OTHER PUBLICATIONS

"Handbook of Plastics Joining: A Practical Guide"; William Andrew, Inc.; 1997; pp. 121-124; Plastics Design Library; New York, USA.

Christians, Rolf, "Membranen in der Pneumatik," *Fluid*, pp. 39-46 (Apr. 1980).

* cited by examiner

CHECK VALVE

CROSS-REFERENCE TO RELATED APPLICATION

This patent application is a continuation-in-part of International Application PCT/EP2005/006425 published as PCT patent application WO 2005/123176 A1, with an international filing date of Jun. 17, 2005 and entitled "NON-RETURN VALVE, PARTICULARLY FOR MEDICAL APPLICATIONS," which claims the benefit of priority to German patent application DE 20 2004 009 521.1, filed Jun. 17, 2004 and entitled "Rückschlagventil, Insbesondere für Medizinische Anwendungen"; and a continuation-in-part of German patent application DE 20 2006 016 730.7, filed Oct. 30, 2006 and entitled "Rückschlagventil, Insbesondere für Medizinische Anwendungen." The entire contents of each of the above applications are incorporated herein by reference.

FIELD OF THE INVENTION

This invention relates to a check valve, such as a check valve suited for medical applications.

BACKGROUND

Check valves may be used to selectively fluidly connect a first hose with a second hose. More specifically, check valves known in the art may be used to permit fluid flow in a first direction and to prevent or restrict flow in a second, opposite direction. One such known check valve includes a first hose connector housing, a second hose connector housing, and a membrane disk of flexible material positioned between the two hose connector housings. The membrane disk is selectively sealingly seated on a valve seat to selectively separate the first and second hoses from each other. Specifically, when unaffected by external forces the membrane disk is seated on the valve seat. However, the membrane disk becomes unseated and permits fluid connection between the first and second hoses when a sufficient external force acts on the membrane disk, such as fluid pressure from fluid flowing along the first hose. More specifically, the membrane disk defines openings located radially outwardly from the valve seat that permit fluid flow therethrough when the membrane disk is unseated, thereby connecting the first and second hoses. Such a design is disclosed European patent 0 612 537, and German Utility Model 20 2004 009 358.8, the entire contents of each of which are incorporated herein by reference.

In the medical technique, check valves may be used for the lines of infusion systems, syringes, diagnosis equipment, intravenous hose lines, in connection with syringe pumps, and the like. Check valves used for medical applications preferably have closing times of a few fractions of a second and are able to close safely to avoid any reflux of possibly contaminated fluids. Therefore, such check valves are preferably statistically accurate. Additionally, because check valves used in medical applicants are typically a single-use product, such check valves are also preferably relatively inexpensive and easy to manufacture.

Furthermore, medical and/or governmental regulations and/or other legal provisions and standards may require uniform safety functions. For example, in Germany, medical devices must be approved before they are able to be generally used in medical applications.

One such known check valve design includes a membrane disk with an annular protrusion received within annular grooves defined by the first and second hose connector housings. This design causes the membrane disk to have a relatively, radially-tight fit such that the seal between the membrane disk and the valve seat is relatively consistent, that is, the fluid pressure required to unseat the membrane disk is relatively consistent. Additionally, the radial tension forces acting on the membrane disk cause relatively fast action between the membrane disk and the valve seat.

However, it is desirable to have available check valves of varying opening pressures for different applications and/or for use with patients having varying characteristics. For example in connection with the use of syringe pumps, it is desirable to prevent the pump from running empty due to the difference in height between the patient and syringe pump since the valve could already be open because of the geodetic height. Since such valves however usually are assembled from injection molded parts, the production of valves having different opening pressures may lead to substantial costs of the molds.

During use of known check valves, relatively high fluid pressure from the entry hose may cause the membrane disk to be unseated by an undesirable distance, such that the openings in the membrane disk contact a wall of the second tube connector housing and are obstructed or partially obstructed, thereby undesirably blocking or restricting fluid flow to the second hose.

It is therefore desirable to provide a check valve that meets medical and legal standards, that is relatively simple and economical to manufacture, that may be manufactured with varying characteristics in a simple and economical manner, and that prevents or minimizes undesired closing of the check valve due to relatively high entry pressures or high differential pressures.

BRIEF SUMMARY

This invention seeks to address the above-mentioned shortcomings of the prior art. A check valve is provided, including a first hose connector housing defining an entry passage extending into an entry space at least partially defined by an annular valve seat, a second hose connector housing coupled with the first hose connector housing and defining an exit passage, and a generally flexible membrane disk positioned between the first and second hose connector housings such that the membrane disk selectively engages the valve seat. The second hose connector housing defines a protrusion extending generally toward the entry passage to urge the membrane disk towards the entry passage. The membrane disk defines at least one opening located radially outwardly from the valve seat, and the membrane disk is configured to be movable between a seated position, where the entry space and the exit passage are fluidly sealed from each other, and an unseated position, where the entry space and the exit passage are fluidly connected via the at least one opening. The valve seat is located radially outwardly from the protrusion such that an unseating pressure required to move the membrane disk from the seated position to the unseated position is at least partially determined by the radial distance between the valve seat and the protrusion.

In one aspect, the protrusion is configured to permit fluid flow from the opening in the membrane disk to the exit passage. Additionally, the second hose connector housing may define a plurality of protrusions each extending generally toward the entry passage.

In another aspect, the projections are positioned with respect to each other such as to surround the exit passage. For example, the projections may define a generally crown-shaped formation. Additionally, the projections and the second hose connector housing may be formed as a single, unitary component. The membrane disk may include an annular protrusion at an outer circumference thereof configured to be received in annular grooves defined by the first and second hose connector housings.

In another aspect, a check valve is provided, including a first hose connector housing defining an entry passage extending into an entry space at least partially defined by an annular valve seat, a second hose connector housing coupled with the first hose connector housing and defining supporting surfaces, and a generally flexible membrane disk positioned between the first and second hose connector housings such that the membrane disk selectively engages the valve seat. The second hose connector housing defines an exit passage, a plurality of supporting surfaces, a recess, and a groove fluidly connecting the recess with the exit passage. The membrane disk defines at least one opening located radially outwardly from the valve seat, and the membrane disk is configured to be movable between a seated position, where the entry space and the exit passage are fluidly sealed from each other, and an unseated position, where the entry space and the exit passage are fluidly connected via the at least one opening. When the membrane disk is unseated and the entry-side fluid pressure is relatively high, the membrane disk engages the supporting surfaces and is thereby prevented from undesirably high deflection.

In yet another aspect, the second hose connector housing defines a plurality of recesses respectively positioned between adjacent supporting surfaces and a plurality of grooves each fluidly connecting one of the recesses with the exit passage. The supporting surfaces each preferably extend generally radially towards an outer rim of the second hose connector housing. The supporting surfaces may also define a broadening width along a direction toward an outer rim of the second hose connector housing. Additionally, each of the grooves is preferably positioned between adjacent supporting surfaces.

In another aspect the membrane disk defines a plurality of openings located radially outwardly from the valve seat and wherein each of the openings is generally kidney-shaped. Additionally, the second hose connector housing preferably defines six supporting surfaces and the membrane disk preferably defines eight openings.

In yet another aspect the supporting surfaces each define an inner end positioned within a radius of the valve seat and the inner ends each define a projection positioned within the radius of the valve seat and configured to pretension the membrane disk towards the valve seat.

In another aspect, the second hose connector housing includes an outer rim configured to secure the membrane disk and the supporting surfaces each define a first portion extending substantially completely across a radial distance between the exit passage and the outer rim. The second hose connector housing may also include an outer rim configured to secure the membrane disk and wherein the supporting surfaces each define a first portion extending substantially completely across a radial distance between the exit passage and the outer rim. The supporting surfaces each preferably further define a second portion extending across a portion of the radial distance between the exit passage and the outer rim. Additionally, the supporting surfaces each preferably define a generally concave surface.

DETAILED DESCRIPTION OF THE DRAWINGS AND THE PRESENTLY PREFERRED EMBODIMENTS

Figure 1:
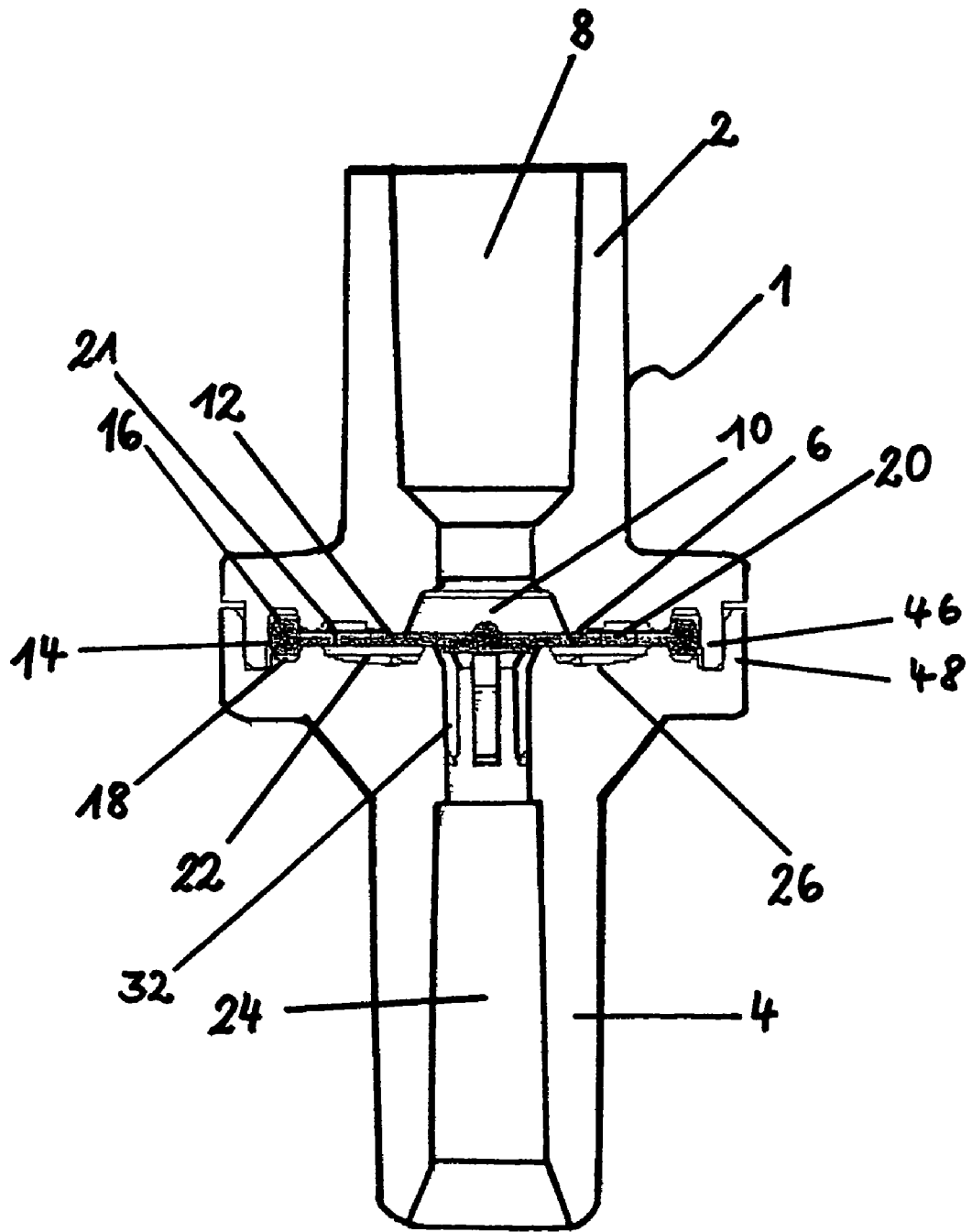
FIG. 1 is a partial-section, schematic view of an embodiment.

Referring now to preferred embodiments, FIG. 1 shows a check valve 1 that is preferably especially suitable for medical applications and that preferably is suitable for use with relatively high-pressure flow (such as 25 bars) and for use with relatively low-pressure flow (such as 0.5 bars). The check valve 1 includes a first hose connector housing 2 and a second hose connector housing 4 and a membrane disk 6 positioned between the two hose connector housings 2 and 4. The hose connector housings 2, 4 are each preferably injection-molded from a plastic material, such as a medically accepted plastic, e.g. polystyrenes, styrenic copolymers (A.B.S.), or polycarbonates, and the membrane disk is preferably made of a flexible plastic material such as silicone, silicone rubber, or rubber.

The first hose connector housing 2 includes an entry passage 8 opening into an entry chamber 10. The entry chamber 10 is surrounded by an annular valve seat 12 against which the membrane disk 6 is pretensioned.

The membrane disk 6 includes a completely closed center section such that substantial tension forces can be transferred from the center outwardly and vice versa. The outer circumferential area the membrane disk 6 is provided with an annular bulge 14 that is preferably unitarily formed with the body of the membrane disk 6 via a suitable method such as injection-molding. In the front face of the first hose connector housing 2, an annular groove 16 is formed. Additionally, in the front face of the second hose connector housing 4, a corresponding annular groove 18 is formed. During the assembly of the first hose connector housing 2 with the second hose connector housing 4, the annular bulge 14 is received in the two oppositely arranged annular grooves 16 and 18 of the two hose connector housings 2 and 4 and is simultaneously pretensioned against the valve seat 12.

Figure 2:
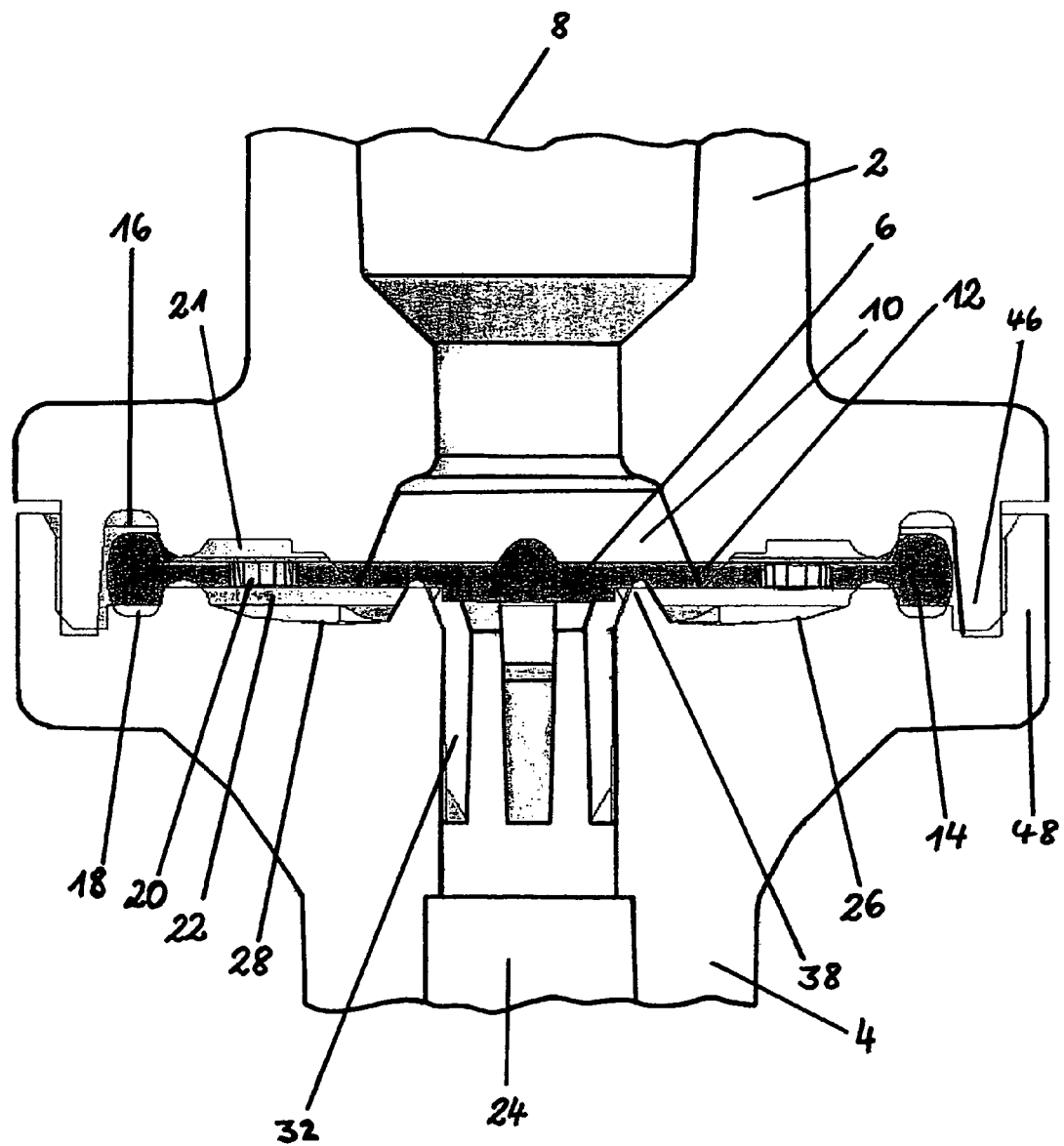
FIG. 2 is an enlarged view of the check valve shown in FIG. 1.

As best shown in FIG. 2, the membrane disk 6 includes openings 20 located radially outwardly of the valve seat 12. Therefore, when the membrane disk 6 is unseated from the valve seat 12, the openings are able to connect an annular chamber 21 positioned radially outward of the valve seat 12 in the first hose connector housing 2 with an exit chamber 22 in the second hose connector housing 4 which is connected with the exit passage 22 of the second hose connector housing 4.

The exit chamber 22 includes a wall 26 oppositely positioned with respect to the openings 20 of the marginal area of the membrane disk 6 in which recesses generally designated with 28 are provided which are oppositely arranged with respect to the openings 20. The recesses 28 are separated from each other by supporting surfaces 30 for the membrane disk, wherein the recesses 28 are connected with the exit passage 24 by narrow deep grooves 32. The supporting surfaces 30 prevent the membrane disk 6 from deflecting an undesirably high distance to prevent the openings 20 from being obstructed or blocked by the wall 53 of the exit chamber 22. Therefore, the grooves 32 and the supporting surfaces 30 cooperate to facilitate use of the check valve 1 under high differential pressure. For example, the grooves and the supporting surfaces 30 prevent over deflection of the membrane disk 6 and permit the fluid to flow through the check valve 1 at a desired, relatively high flow rate.

Figure 3:
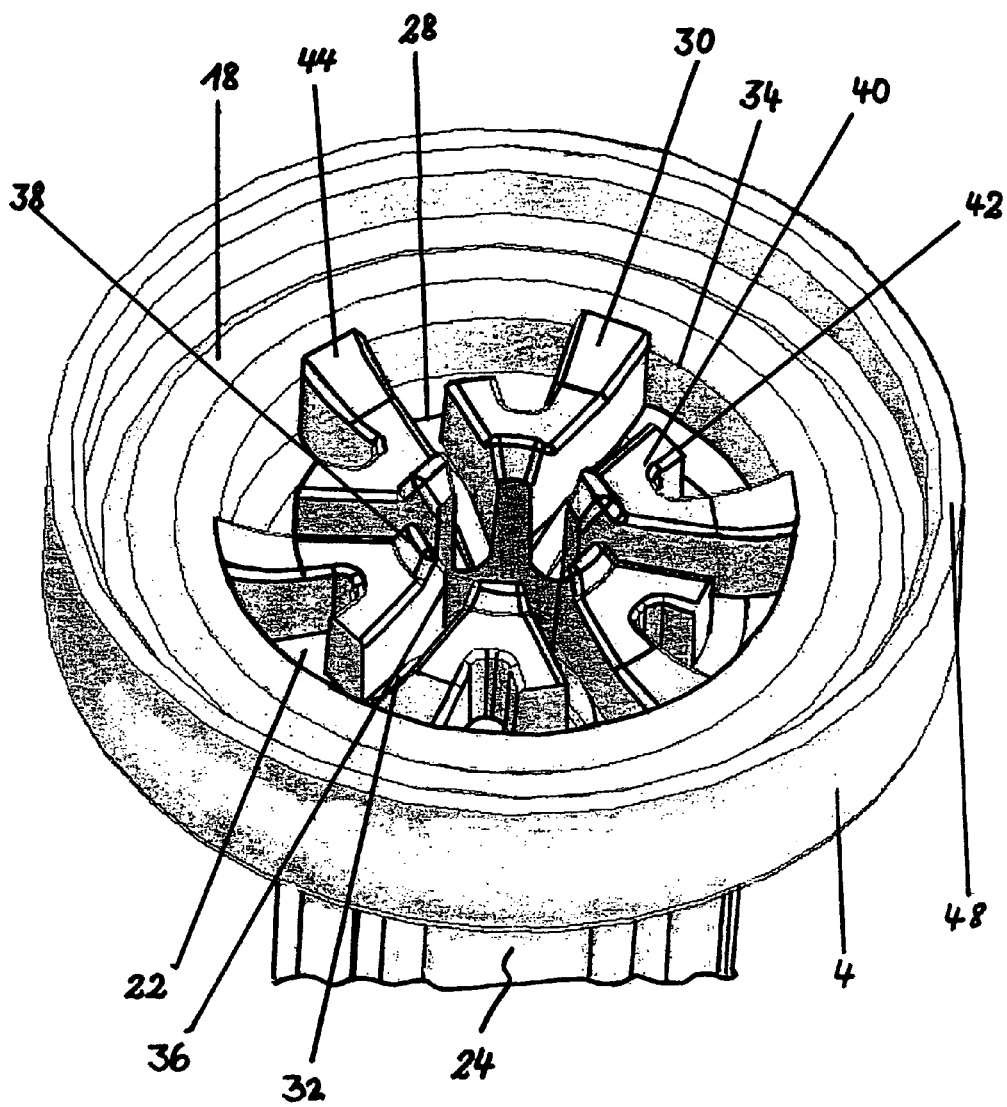
FIG. 3 is an enlarged, perspective view of a second hose connector housing of the valve shown in FIG. 1.
Figure 4:
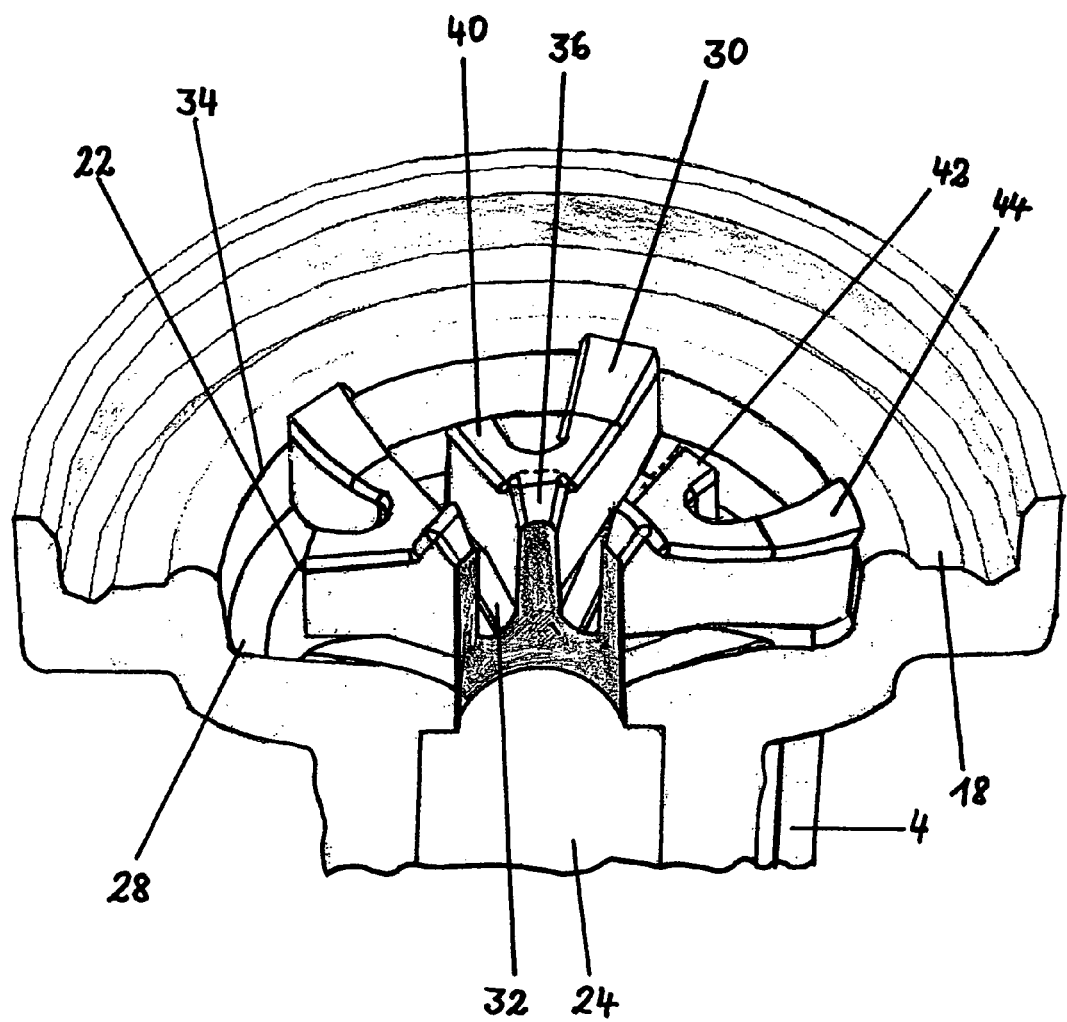
FIG. 4 is an enlarged, perspective view of the second hose connector housing as shown in FIG. 3, with a portion of valve removed for illustrative purposes.
Figure 5:
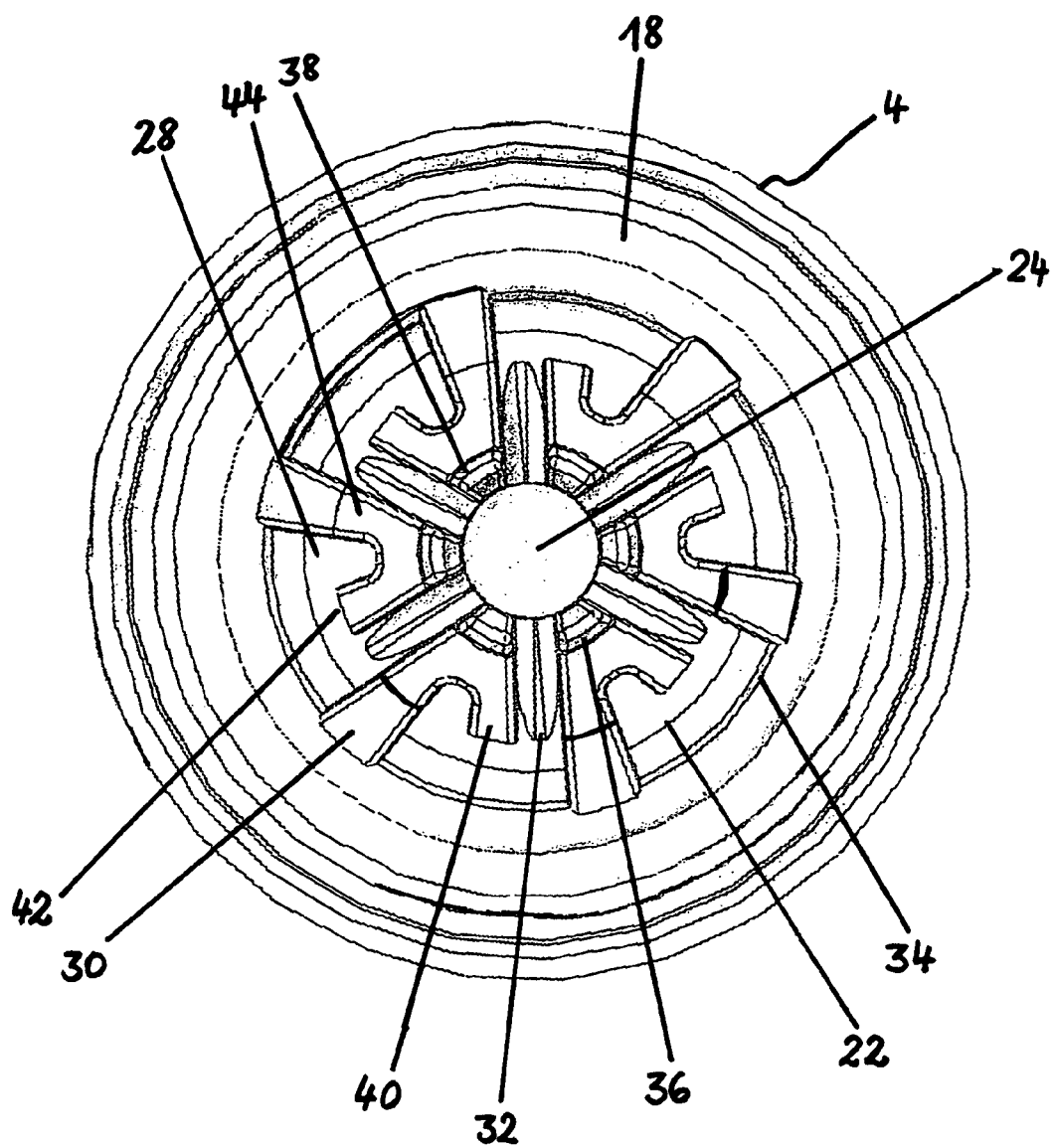
FIG. 5 a top view of the second hose connector housing in FIG. 3.

As best shown in FIGS. 3 through 5, the supporting surfaces 30 preferably extend from a radially central portion of the exit chamber 22 to the outer rim 34 of the exit chamber 22. Additionally the supporting surfaces 30 preferably have increasing widths in the direction of the outer rim 34 such that as large of an area as possible may be available for the possible contact with the membrane disk 6 at high pressures.

The supporting surfaces 30 shown in the figures also include inner ends 36 positioned within the radius of the opposed valve seat 12. The inner ends 36 of the supporting surfaces 30 preferably include projections 38 positioned within the radius of the valve seat 12 and extending in the direction of the membrane disk 6. The projections thereby contact the membrane disk 6 and hold or pretension the same in the direction of the entry chamber 10. The projections 38 surround the entry opening of the exit passage 24 starting out from the exit chamber 22 in an annular pattern with spaces therebetween. The projections 38 and the supporting surfaces 30 are preferably unitarily formed by a suitable process such as injection-molding. By means of the height of the projections 38, an opposing pretension is created with respect to the membrane disk 6, wherein by changing the height of the projections 38 a change of the cracking or unseating pressure of the check valve can be achieved.

As best shown in FIGS. 3 to 5, the supporting surfaces 30 may be provided with additional surfaces 40 projecting from the inner ends 38 laterally and at an acute angle with the radial outer ends 42 thereof lying within the radius on which the openings 20 in the membrane disk 6 are positioned. The additional surfaces 40 provide an additional support for the membrane disk 6 at high pressures, particularly in the radial inner area where the membrane disk 6 may experience particularly high loads. Additionally, the surfaces 44 of the supporting surfaces 30 and the additional surfaces 40 opposite to the membrane disk are preferably concavely shaped and therefore are corresponding to the shape of the membrane disk under high pressure during the opening of the valve.

As best shown in FIGS. 2 to 5, the deep and narrow grooves 32 are each positioned between a supporting surface 30 and the additional surface 40 of the neighboring supporting surface 30 such that fluid is able to flow through the openings 20 into the exit chamber 22 in an unobstructed manner.

For simplifying the assembly of the check valve 1, namely to avoid the demand of a special orientation of the membrane disk 6, the openings 20 in the membrane disk 6 are kidney-shaped. Further the check valve 1 preferably includes six supporting surfaces 30 with the corresponding additional surfaces 40 and the membrane disk 6 preferably includes eight kidney-shaped openings 20.

For the assembly the two hose connector housings 2 and 4 can be connected by interconnecting an inner annular projection 46 on the first hose connector housing 2 and an outer annular projection 48 on the second hose connector housing 4. The projections 46, 48 are preferably connected by a suitable method such as welding, ultrasonic welding, or gluing.

During operation of the check valve, when a relatively high entry-side pressure acts on the membrane disk 6, the membrane disk 6 contacts the supporting surfaces 30 and additional surfaces 40 and is thereby prevented from contacting the wall 26. This design reduces excessive strain or deformation and maintains fluid connection between the entry chamber 10 and the exit chamber 22.

Figure 6:
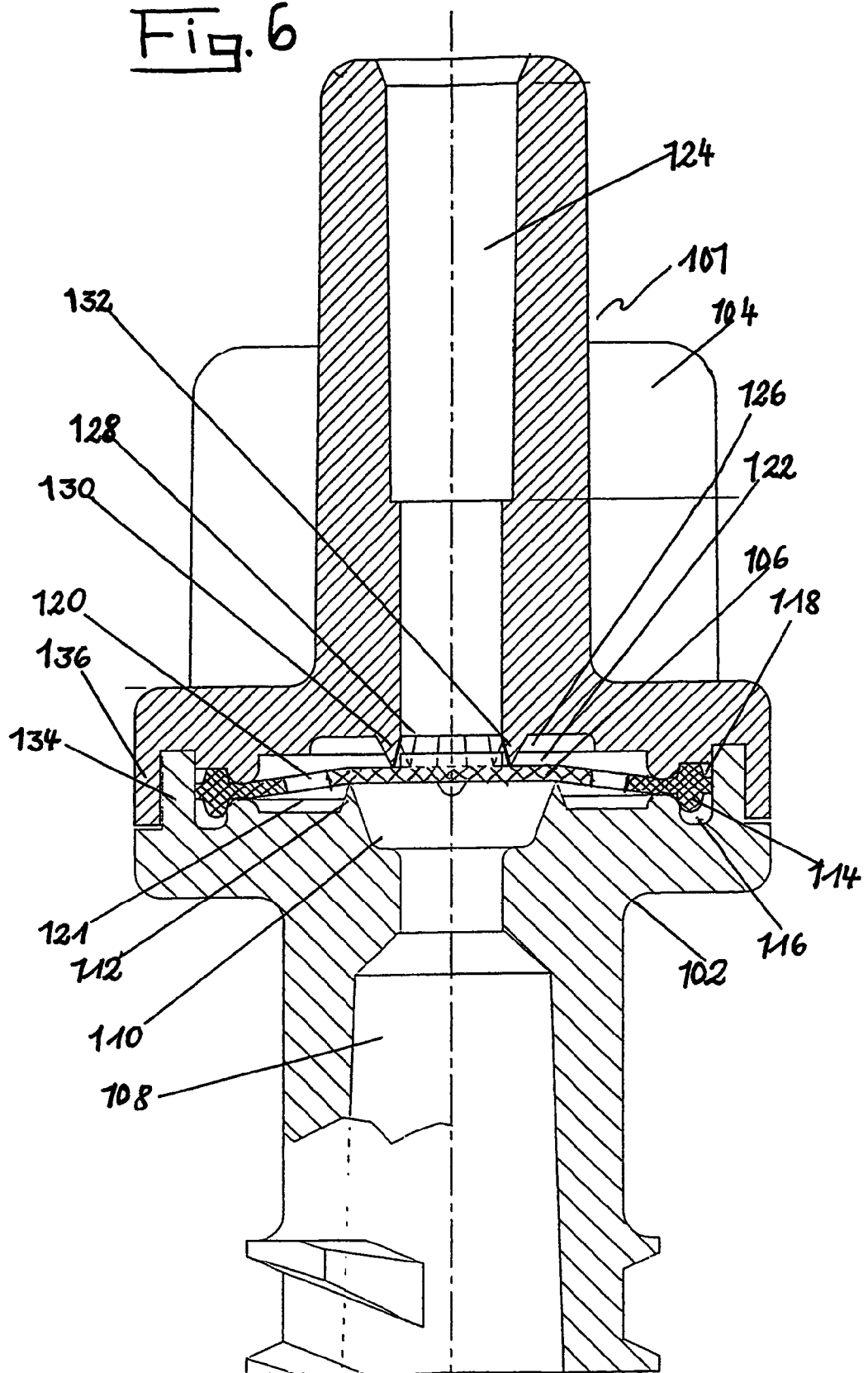
FIG. 6 is a partial-section, schematic view of another embodiment.

Referring now to FIG. 6, another embodiment is shown. The check valve 101 shown in FIG. 6 is especially suitable for medical use. The check valve 101 includes a first hose connector housing 102, a second hose connector housing 104 which, and a membrane disk 106 positioned and clamped therebetween. The housings 104, 106 may be produced by a suitable method such as injection molding from plastics like that of the first embodiment and the membrane disk 6 is preferably made of a flexible material like that of the first embodiment, such as silicone, silicone rubber, or rubber.

The first hose connector housing 102 includes a first entry passage 108 leading to an entry space 110. The entry space 110 is surrounded by an annular valve seat 112 against which the membrane disk 106 is pretensioned. At the outer circumferential area of the membrane 106, an annular protrusion 114 is provided and is positioned between an annular groove 116 of the first hose connector housing and an annular groove 118 of the second hose connector housing 102. During the assembly of the first hose connector 102 housing with the second hose connector housing 104, the annular protrusion 114 is received within the two oppositely positioned annular grooves 116 and 118 and the membrane disk 106 is pretensioned against the valve seat 112.

The membrane disk 106 includes openings 120 positioned radially outwardly from the valve seat 112 to selectively connect an annular space 121 of the first hose connector housing 102, which is radially exterior of the valve seat 112, with an exit space 122 of the second hose connector housing 104, the latter being connected with an exit passage 124 of the second hose connector housing 104.

The wall 126 of the second hose connector housing 4 is positioned opposite the membrane disk 106 and limits the exit space 122 in the upward direction. A projecting formation generally designated with 128 is formed on the wall 126. The formation 128 is preferably pervious to media. The formation 128 supports the membrane disk 106 and/or pretension the membrane disk 106 in the direction of the entry space 110. As shown, the formation 128 is positioned within the radial boundary of the valve seat 112.

The formation 128 in FIG. 6 includes a number of projections 130. More specifically, the formation 128 in FIG. 6 defines a series of discontinuous circumferential projections 130 extending generally toward the entry space 110. The projections 130 are circumferentially generally equally spaced from each other such that the circumferential distance between any two adjacent projections 130 is generally constant. Additionally, the projections 130 are preferably in the shape of a crown and are surrounding the entry opening 132 of the exit passage starting from the exit space. As shown, the projections 130 are preferably unitarily formed with the second hose connector housing 104 by a suitable method such as injection molding. The height of the projections 130 affects the force exerted on the oppositely pretensioned membrane disk 106. Therefore, the force exerted on the membrane disk 106 by the projections 130 may be modified by adjusting the height of the projections 130. As an alternative it is also possible to modify the radial distance between the valve seat 112 and the projections 130 to adjust the force exerted on the membrane disk 106 by the projections 130. More specifically, by adjusting the radial distance between the valve seat 112 and the projections 130, the lever between these components is adjusted. These design modifications also affect the unseating pressure required to unseat the membrane disk 106.

For the assembly the two hose connector housings 102 and 104 can be connected by interconnecting an inner annular projection 134 on the first hose connector housing 104 and an outer annular projection 136 on the second hose connector housing 104. The projections 134, 136 are preferably connected by a suitable method such as welding, ultrasonic welding, or gluing.

It is therefore intended that the foregoing detailed description be regarded as illustrative rather than limiting, and that it be understood that it is the following claims, including all equivalents, are intended to define the spirit and scope of this invention. More particularly, the apparatus and assembly described are merely an exemplary apparatus and assembly, and they are not intended to be limiting. Many of the steps and devices for performing the steps described above may be eliminated or replaced by alternative steps and devices.

What is claimed is:

1. A check valve for liquid applications comprising:
    a first hose connector housing defining an entry passage extending into an entry space at least partially defined by an annular valve seat;
    a second hose connector housing coupled with the first hose connector housing, the second hose connector housing defining an exit passage, an outer rim, a plurality of supporting surfaces spaced circumferentially about the exit passage the supporting surfaces defining recesses therebetween, and at least one groove fluidly connecting at least one recess with the exit passage, the second hose connector housing defining a series of discontinuous protrusions spaced circumferentially about the exit passage and extending generally toward the entry passage; and
    a generally flexible membrane disk clamped between the first and second hose connector housings such that the membrane disk engages the protrusions and selectively engages the valve seat, the membrane disk defining at least one opening located radially outwardly from the valve seat, where the membrane disk is configured to be movable between a seated position, where the entry space and the exit passage are fluidly sealed from each other by the membrane disk, and an unseated position, where the entry space and the exit passage are fluidly connected via the at least one opening;
    wherein the valve seat is located radially outwardly from the protrusions such that the protrusions about the exit passage circumferentially support the membrane disk toward the entry space and pretensions the membrane disk against the valve seat such that an unseating pressure required to move the membrane disk from the seated position to the unseated position is at least partially determined by the radial distances between the valve seat and the protrusions, and wherein the supporting surfaces each define a first radial portion extending substantially along the radial distance between the exit passage and the outer rim and a second radial portion connected to the first radial portion adjacent the exit passage and extending across a portion of the radial distance between the exit passage and the outer rim, thereby defining a second recess between the first radial portion and second radial portion fluidly connected to the recess between supporting surfaces, wherein the membrane disk opening overlies a recess between the first and second radial portions such that the membrane disk at the unseated position under high differential pressures engages the first and second radial portions.

2. A check valve as in claim 1, wherein the protrusions are configured to permit fluid flow from the opening in the membrane disk to the exit passage.

3. A check valve as in claim 2, wherein the protrusions are generally circumferentially equally spaced.

4. A check valve as in claim 3, wherein the protrusions define a generally crown-shaped formation.

5. A check valve as in claim 4, wherein the protrusions and the second hose connector housing are a single, unitary component.

6. A check valve as in claim 1, wherein the coupled first and second hose connector housings define an annular groove of greater diameter than the annulus of the valve seat, and the membrane disk includes an annular protrusion, wherein the disk annular protrusion is configured to be received in the annular groove defined by the coupled first and second hose connector housings.

7. A check valve for liquid applications comprising:
    a first hose connector housing defining an entry passage extending into an entry space at least partially defined by an annular valve seat;
    a second hose connector housing coupled with the first hose connector housing, the second hose connector housing defining an exit passage, an outer rim, a plurality of supporting surfaces spaced circumferentially about the exit passage, wherein each supporting surface includes a projection located within the diameter of the annular valve seat and extending generally toward the entry passage and further includes a first radial portion extending substantially along the radial distance between the exit passage and the outer rim, the supporting surfaces defining recesses therebetween, and at least one groove fluidly connecting at least one recess with the exit passage; and
    a generally flexible membrane disk clamped between the first and second hose connector housings such that the membrane disk engages the supporting surface projections to pretension the membrane disk against the valve seat and selectively engage the valve seat, the membrane disk defining at least one opening located radially outwardly from the valve seat, where the membrane disk is configured to be movable between a seated position, where the entry space and the recess are fluidly sealed from each other, and an unseated position, where the entry space and the recess are fluidly connected via the at least one opening such as to fluidly connect the entry passage with the exit passage;
    wherein the membrane disk is positioned such that at least one membrane disk opening overlies at least one recess in the second hose connector housing and the membrane disk at the unseated position under high differential pressures engages the first radial portions and fluidly connects the entry space with the exit passage via the at least one membrane disk opening, the recess, and the groove in the second hose connector housing, and wherein the supporting surfaces each further define a second radial portion connected to the first radial portion adjacent the exit passage and extending across a portion of the radial distance between the exit passage and the outer rim, thereby defining a second recess between the first radial portion and second radial portion fluidly connected to the recess between supporting surfaces, wherein the membrane disk opening overlies the recess between the first and second radial portions such that the membrane disk at the unseated position under high differential pressures engages the first and second radial portions of the supporting surface projections to thereby fluidly connect the entry space with the exit passage via the membrane disk opening, the recess between the first and second radial portions, the recess between supporting surfaces and the groove in the second hose connector housing.

8. A check valve as in claim 7, wherein the second hose connector housing defines a plurality of recesses respectively positioned between adjacent supporting surfaces and a plurality of grooves each fluidly connecting one of the recesses with the exit passage.

9. A check valve as in claim 8, wherein the supporting surfaces each extend generally radially to the outer rim of the second hose connector housing.

10. A check valve as in claim 9, wherein the supporting surfaces define a broadening width along a direction toward an outer rim of the second hose connector housing.

11. A check valve as in claim 8, wherein each of the grooves is positioned between adjacent supporting surfaces.

12. A check valve as in claim 8, wherein the membrane disk defines a plurality of openings located radially outwardly from the valve seat and wherein each of the openings is generally kidney-shaped.

13. A check valve as in claim 12, wherein the second hose connector housing defines six supporting surfaces and the membrane disk defines eight openings.

14. A check valve as in claim 7, wherein the supporting surface projections are positioned on the inner end of the supporting surface and adjacent to the exit passage, and positioned within a radius of the valve seat.

15. A check valve as in claim 7, wherein the supporting surfaces each have at least a portion that define a generally concave surface.

16. A check valve as in claim 7, wherein the coupled first and second hose connector housings define an annular groove of greater diameter than the annulus of the valve seat, and the membrane disk includes an annular protrusion, wherein the disk annular protrusion is configured to be received in the annular groove defined by the coupled first and second hose connector housings.

17. A check valve as in claim 7, wherein the coupled first and second hose connector housings define an annular groove of greater diameter than the annulus of the valve seat, and the membrane disk includes an annular protrusion, wherein the disk annular protrusion is configured to be received in the annular groove defined by the coupled first and second hose connector housings.

18. A check valve as in claim 17, wherein the supporting surfaces each have at least a portion that define a generally concave surface.

* * * * *